US010335793B2

(12) United States Patent
Bache et al.

(10) Patent No.: US 10,335,793 B2
(45) Date of Patent: Jul. 2, 2019

(54) CONNECTOR FOR FLUID CHROMATOGRAPHY

(71) Applicants: Bruker Daltonik GmbH, Bremen (DE); Möller Medical GmbH, Fulda (DE)

(72) Inventors: Nicolai Bache, Odense S (DK); Christoph Gebhardt, Bremen (DE); Ole Bjeld Hoerning, Odense S (DK); Ralph Kikillus, Bremen (DE); Frank Hirmer, Schlitz (DE); Peter Aagaard Nielsen, Marslev (DK)

(*) Notice: Subject to any disclaimer, the term of this patent is extended or adjusted under 35 U.S.C. 154(b) by 417 days.

(21) Appl. No.: 15/060,809

(22) Filed: Mar. 4, 2016

(65) Prior Publication Data
US 2017/0252746 A1   Sep. 7, 2017

(51) Int. Cl.
   *G01N 1/00*    (2006.01)
   *B01L 3/00*    (2006.01)
   *A61M 39/10*   (2006.01)
   *F16L 15/00*   (2006.01)

(52) U.S. Cl.
   CPC ........... *B01L 3/563* (2013.01); *A61M 39/10* (2013.01); *B01L 3/561* (2013.01); *F16L 15/00* (2013.01); *B01L 2200/026* (2013.01); *B01L 2300/0838* (2013.01)

(58) Field of Classification Search
   CPC ................................. G01N 30/6026
   See application file for complete search history.

(56) References Cited

U.S. PATENT DOCUMENTS

| 5,669,637 | A  | 9/1997  | Chitty et al. |
|-----------|----|---------| --------------|
| 6,273,478 | B1 | 8/2001  | Benett et al. |
| 6,575,501 | B1 | 6/2003  | Loy, Jr. |
| 8,696,038 | B2 | 4/2014  | Nienhuis |
| 9,091,693 | B2 | 7/2015  | Hochgraeber et al. |
| 2006/0239863 | A1 | 10/2006 | Zach et al. |
| 2011/0298210 | A1 | 12/2011 | Hochgraeber et al. |
| 2013/0298647 | A1* | 11/2013 | Falk-Jordan .......... F16L 19/061 73/61.55 |
| 2014/0131997 | A1 | 5/2014  | Bürger et al. |

FOREIGN PATENT DOCUMENTS

WO    2012116753 A1    9/2012
WO    2013174421 A1    11/2013

* cited by examiner

*Primary Examiner* — Jyoti Nagpaul
(74) *Attorney, Agent, or Firm* — Benoit & Côté Inc.

(57) ABSTRACT

The invention generally relates to a connector for fluid chromatography, such as gas chromatography and liquid chromatography, having a female assembly including a receiving member being designed and configured to receive, and releasably interlock with, a male assembly. The connector is particularly suited for high performance liquid chromatography (HPLC) applications.

20 Claims, 9 Drawing Sheets

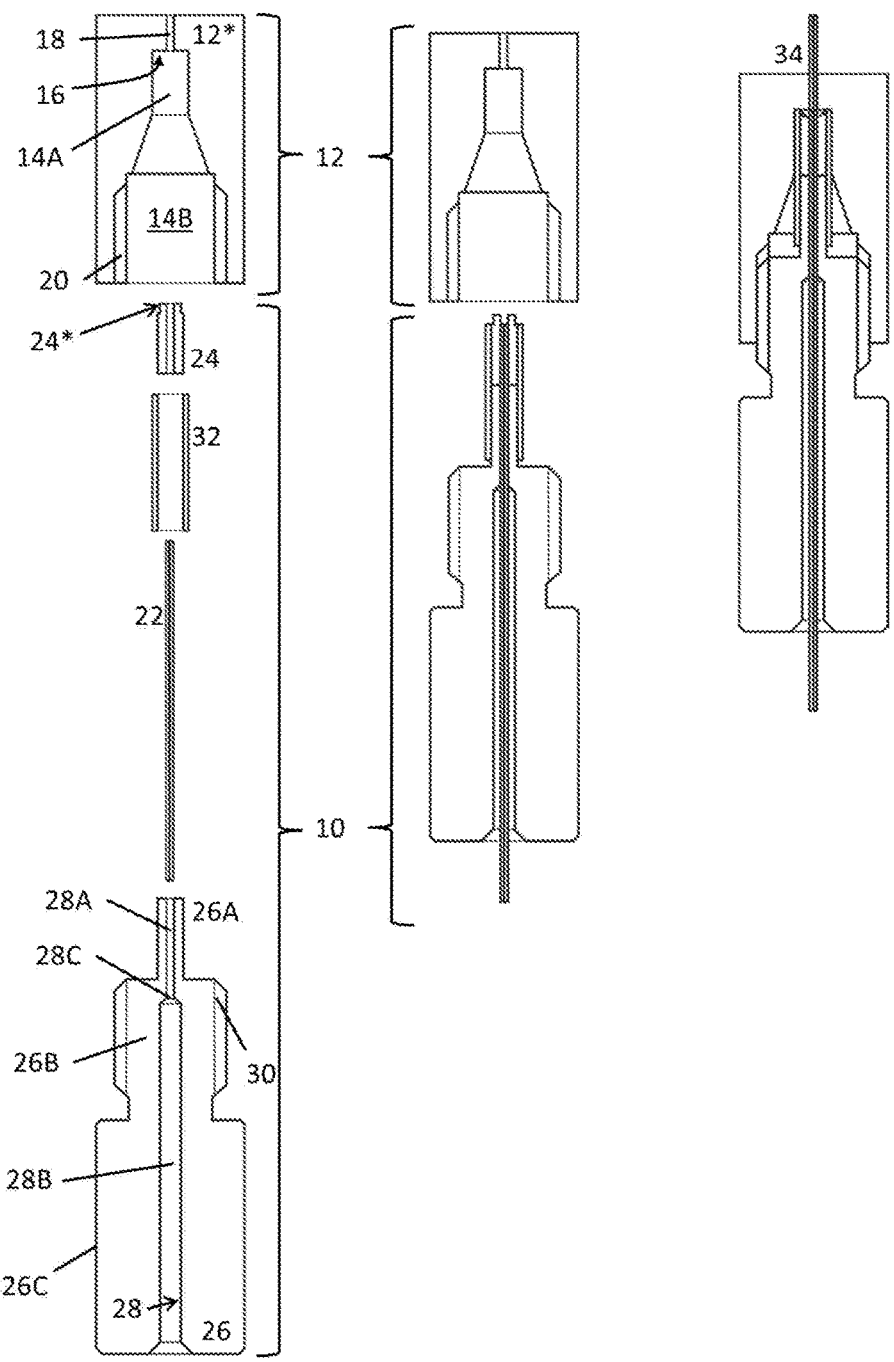
FIGURE 2A   FIGURE 2B   FIGURE 2C

CONNECTOR FOR FLUID CHROMATOGRAPHY

BACKGROUND OF THE INVENTION

Field of the Invention

The invention relates generally to connectors for fluid chromatography, such as gas chromatography (GC) and liquid chromatography (LC), particularly for the high performance regime, such as high pressure liquid chromatography—HPLC.

Description of the Related Art

Various design solutions for fluid connectors in general exist in the state of the art, a selection thereof being summarized in the following.

The international patent application WO 2013/174421 A1 discloses a sealing element for sealing a fluidic connection between a coupling element and a tubular element and is stated to thereby provide a sealed flow path through the tubular element and between the coupling element and the tubular element in a longitudinal direction. The sealing element is stated to comprise a recess extending in the longitudinal direction, wherein the recess is adapted for receiving the tubular element, and a transverse wall defining an extent of the recess in the longitudinal direction, wherein the transverse wall has a through hole.

The international patent application WO 2012/116753 A1 discloses a sealing fluidic component which is stated to comprise a capillary enclosing a fluid conduit and having an exterior surface being at least partially coated with a coating of a meltable material. Further comprised is a sealing at an end portion of the capillary integral with the coating, constituted at least partially by the meltable material, and formed by melting the meltable material of the coating at the end portion and re-solidifying the melted material.

U.S. patent application 2006/0239863 A1 to Zach et al. discloses a line element for handling fluids that is stated to comprise at least one temperature-resistant and pressure-resistant support element having a first interior in which an inner line made of a plastic material resistant to chemicals is arranged. At least one free end of the line element is stated as being provided with a connector element having a second interior into which the inner line extends. The support element or the connector element is stated to have at least one relief opening which ensures a communicating link between the first interior of the support element or the second interior of the connector element and the environment.

U.S. Pat. No. 5,669,637 A to Chitty et al. and U.S. Pat. No. 8,696,038 B2 to Nienhuis generally disclose fitting assemblies.

U.S. Pat. No. 6,273,478 B1 to Benett et al. discloses a miniature connector for transmitting microliter quantities.

U.S. Pat. No. 6,575,501 B1 to Loy Jr. et al. discloses a deformable bushing to seal tubing to a receiving body.

U.S. Pat. No. 9,091,693 B2 to Hochgraeber et al. discloses a plug unit to be connected to a complementary bushing unit for chromatography applications. Essential for the disclosed technical teaching is a pressure piece that is crimped locally into a capillary tube assembly having a sealing element. In order to achieve the sealing between plug unit and bushing unit, pressurization forces are stated to be transmitted from the plug housing via the pressure piece toward the sealing element.

In view of the above, there is still a need for improvement with connectors for fluid chromatography, such as gas chromatography and liquid chromatography.

SUMMARY OF THE INVENTION

The invention relates generally to a connector for fluid chromatography. The connector has a female assembly with a receiving member being designed and configured to receive, and releasably interlock with, a male assembly. The male assembly comprises a force-transmitting member for exerting axial pressurization, further a capillary conduit reaching slidably through a passage in the force-transmitting member for transmitting chromatography fluid, yet further a sealing gasket surrounding a front end of the capillary conduit, the sealing gasket having a rearward facing surface located such as to directly contact a forward facing surface of the force-transmitting member for being subjected to axial pressurization thereby, and a jacket surrounding the sealing gasket for providing axial guidance and alignment thereto.

The force-transmitting member pressing against the sealing gasket directly, upon engaging the male assembly with the female assembly, without the aid of any additional force conveying means has the benefit that the axial forces employed for generating the seal are exerted in a very homogeneous manner about the circumference of the capillary conduit which strengthens and generally improves the sealing effect.

Preferred applications for such designs include nanoflow HPLC, using flow rates between about 1 to 1000 nanoliters per minute, and high flow HPLC, using flow rates of about one microliter per minute and above. Operating pressures may range from 5 to 300 bar and above, as may correlate to ultra performance LC (UPLC) and ultra high performance LC (UHPLC) where typical pressures can be in the range up to or even above 1000 bar.

In various embodiments, the force-transmitting member may comprise a stepped member having a first portion for exerting axial pressurization featuring a first outer diameter, and having a second axially adjacent portion featuring a second outer diameter being larger than the first outer diameter.

In various embodiments, the forward facing surface may be located at a front end of the first portion of the stepped member, the first portion being dimensioned such by axial length and diameter that it can be largely slidably received within a rear part of the jacket. The jacket's inner diameter can be in the lower millimeter range, such as between 0.5 and two millimeters, for example.

In various embodiments, a shape of the sealing gasket, the first portion of the stepped member and the jacket are preferably substantially annular cylindrical generally improving the ease-of-production of these elements of the male assembly.

In various embodiments, the connector may further comprise a third portion being located axially adjacent to the second portion of the stepped member for finger tightening a connection between the male and female assemblies, a third outer diameter of the third portion being larger than that of both the first and second portions. In order to render an improved haptic experience to an operator of the connector, an outer circumferential surface of the third portion can be textured, such as being provided with a knurl. The possibility to finger tighten the male assembly in the female assembly generally dispenses with the need for additional tools, such as wrenches, to establish the connection. In this manner the handling of the connector is simplified.

In various embodiments, axial lengths of the sealing gasket, the first portion of the stepped member and the surrounding jacket can be dimensioned such that a rearward-facing end of the jacket stays clear from a transition between the first portion and second portion of the stepped member.

In various embodiments, the connector may further comprise a constriction foreseen in the passage of the stepped member, wherein the capillary conduit has an outer coating layer (or additional protective tubing) at a position spaced apart from its front end, the coating layer (or protective tubing) being designed and configured to engage with the constriction and further having the function of a limit stop in order to limit axial movability of the stepped member relative to the capillary conduit. Moreover, this limit stop function helps avoid the male assembly becoming stuck in the female assembly, thereby facilitating its pulling out, and further prevents the capillary conduit from being pressed against the bottom of the one-sided port in a damagingly vigorous manner.

In certain embodiments, the first outer diameter of the first portion of the stepped member is preferably slightly undersized compared to that of the sealing gasket, so as to be slidably insertable into the jacket from behind. The magnitude of the undersize can be in the range of several hundred micrometers, such as 300 micrometers, for instance.

In various embodiments, a rearward facing front end of the sealing gasket that comprises the rearward facing surface stays free from being covered by the jacket and directly contacts a forward facing ground of a recess worked into the first portion of the stepped member with which the sealing gasket and jacket partly engage.

In various embodiments, the sealing gasket may stand out slightly from the front end of the capillary conduit in a disengaged condition of the male and female assemblies, and becomes compressed into a substantially flush alignment with the front end of the capillary conduit when the male and female assemblies are engaged with one another. Alternatively, it is also possible to arrange already for a flush alignment in the disengaged condition of the male and female assemblies. For certain embodiments, it might even be conceivable to arrange for the front end of the sealing gasket to be slightly retracted in the disengaged condition from a front end plane established by the capillary conduit and/or the co-extensive jacket. Upon pressurization from behind, the sealing gasket could then slightly bulge forward at the front end, thereby closing the gap to the front end plane and providing for a flush and tight seal.

In certain embodiments, a front end of the sealing gasket can be stepped such as to allow material deformation of the sealing gasket to occur substantially without any outward bulging, which generally may lead to a neater and more reliable sealing effect. A diameter reduction of the sealing gasket's front end, for example, entails pressurization force amplification at the interface where the seal is effected.

In various embodiments, a shape of the force-transmitting member can be substantially annular cylindrical, wherein an outer diameter of the force-transmitting member is slightly undersized compared to that of the sealing gasket in order that force transmission takes place only between the force-transmitting member and the sealing gasket without involving other elements of the connector.

In various embodiments, the receiving member can be one of a one-sided port and a double-sided union. In case of the one-sided port variant, it may have a doubly stepped circular recess, the inner diameter of the first recess step being adapted to the outer diameter of the jacket, and the inner diameter of the second recess step being larger than that of the first recess step. In certain embodiments, it can be adapted to a second outer diameter of a second portion of the stepped member, as described previously. In the case of the double-sided union variant, the aforementioned design features could just be mirrored and reproduced in an abutting (and opposing) relation as will become apparent from embodiments to be described further below.

In certain embodiments, a transition between the second recess step and the first recess step preferably has a conical shape, though it is also conceivable to design it with a perpendicular edge relative to the axis of the connector, for instance.

In some embodiments, both the second recess step and the second portion of the stepped member can have complementary interlocking mechanisms. One example of an interlocking mechanism would comprise an external thread foreseen at an outer circumferential surface of the second portion of the stepped member and a complementary internal thread foreseen at an inner circumferential surface of the second recess step. Other interlocking mechanisms are likewise conceivable, such as a bayonet fitting, for instance, and will be implemented by a skilled practitioner as is deemed fit.

In various embodiments, the one-sided port may have an axial through-bore located such that it comes to rest in opposing relation to the front end of the capillary conduit when the male and female assemblies are engaged with one another.

In various embodiments, the axial through-bore of the one-sided port can accommodate tubing that functions as a continuation of the capillary conduit when the male and female assemblies are engaged with one another. In the simplest example, the tubing is of the same design and configuration as the capillary conduit, such as fused silica capillary, in order to render a good geometric match of the two abutting front ends.

In various embodiments, the one-sided port may have a substantially flat bottom against which a front end of the male assembly is pressed when the male and female assemblies are engaged with one another. Such design ensures that the sealing is effected in the plane of the interface between the capillary conduit and any downstream tubing being coupled thereto, contrary to embodiments where the sealing is effected by means of two opposing frusto-conical surfaces of a complementary nut and ferrule assembly. The main advantage of such bottom seal over a ferrule seal is basically the lower dead volume.

In various embodiments, the sealing gasket may be jointed radially outward to the jacket as well as radially inward to the capillary conduit via opposing outward-facing and inward-facing surfaces, respectively. Preferably, the joint is, or the joints are, produced by one of adhesive, radial swaging, radial plastic deformation, hammering, and laser welding or any combination of these techniques. A skilled practitioner will understand that the heat necessary for welding can be generated by other means than just laser radiation. The joint serves to render the elements thusly jointed unmovable relative to one another even when exposed to external strain, such as axial pressurization of the sealing gasket by the first portion of the stepped member, for example.

In various embodiments, the connector may further comprise a hollow handling shell into which the force-transmitting member is partly accommodated thereby simplifying the manual handling of the connector. In certain embodiments, a second portion of the stepped member may be slidably accommodated in the hollow handling shell. In some cases, for example when a stepped member takes the shape of a T-shaped washer, it can be slidably accommodated fully within the hollow handling shell.

The hollow handling shell preferably comprises a first section with an interlocking mechanism designed and configured to cooperate with a complementary interlocking mechanism foreseen at the receiving member, such as the one-sided port or double-sided union, and further preferably comprises a second section for finger tightening the male assembly in the female assembly.

In certain embodiments, the hollow handling shell can further comprise an inward-protruding edge being designed and configured to engage with a second portion of the stepped member and further having the function of a limit stop in order to keep the stepped member from exiting the cavity of the hollow handling shell.

BRIEF DESCRIPTION OF THE DRAWINGS

The invention can be better understood by referring to the following figures. The elements in the figures are not necessarily to scale, emphasis instead being placed upon illustrating the principles of the invention (often schematically). In the figures, corresponding parts are generally designated by identical last two digits of the reference numerals throughout the different views.

FIGS. 2A to 2C schematically show a first embodiment of a connector according to principles of the invention.

DETAILED DESCRIPTION

While the invention has been shown and described with reference to a number of different embodiments thereof, it will be recognized by those skilled in the art that various changes in form and detail may be made herein without departing from the scope of the invention as defined by the appended claims.

Fluid connectors are designed and configured to establish a fluid communication between an upstream device and a downstream device via intermediate fluid conduits. The upstream device may be a gas or liquid chromatograph or, more specifically, the associated chromatographic column that outputs an eluent of substances which have been separated chromatographically. The downstream device may be a mass spectrometer or, more specifically, the ion source thereof, such as an electrospray ion source. A skilled practitioner is familiar with such kind of instrumentation so that there is no need to elaborate thereon in further detail here. It is to be understood that a chromatography fluid will comprise a mobile phase, in the case of liquid chromatography usually made up of a suitable solvent, into which the sample to be analyzed has been spiked upstream of the chromatographic column.

Figure 1A:
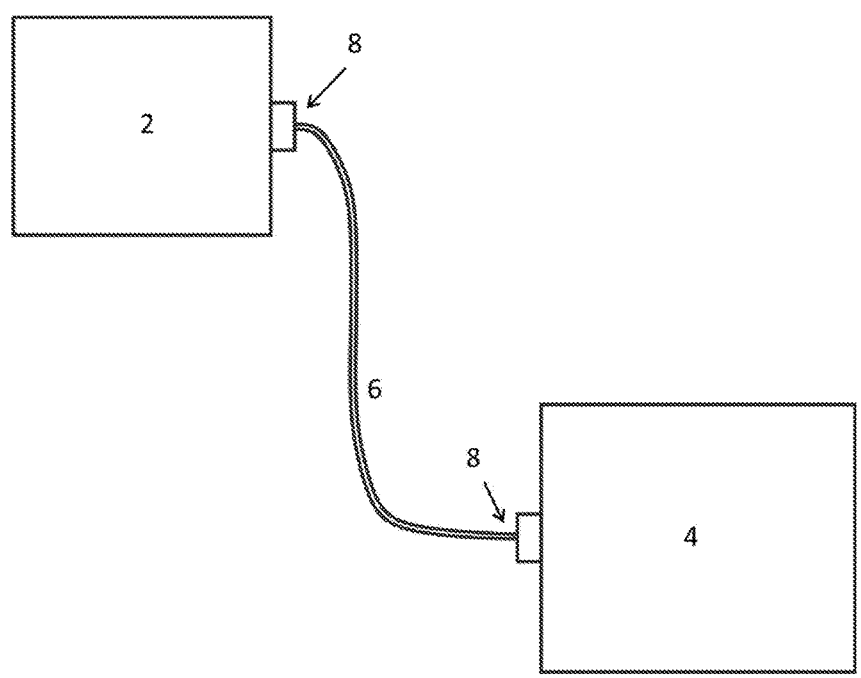
FIGS. 1A and 1B illustrate schematically a fluid connection between an upstream device, such as a gas or liquid chromatograph, and a downstream device, such as an ion source of a mass spectrometer.

FIG. 1A schematically shows by way of example an upstream device 2, such as a gas or liquid chromatograph, and a downstream device 4, such as a mass spectrometer, which are both fluidly connected to one another by means of a conduit 6. The conduit 6 may be flexible and coupled to the two devices 2, 4 by virtue of fluid connectors 8. Such connectors may be designed according to principles of the present invention to be expounded in the following.

Figure 1B:
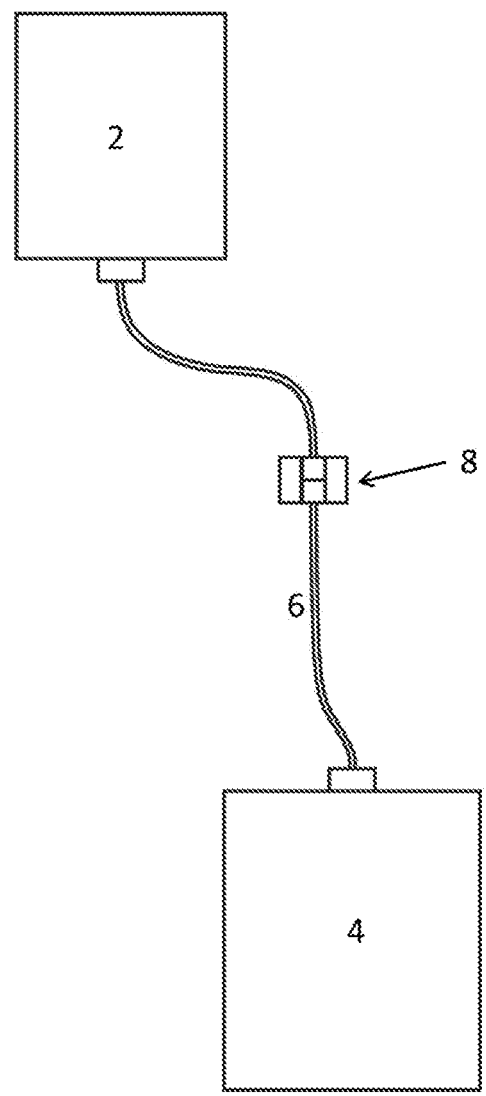

FIG. 1B illustrates a connector 8 of slightly different design where a union receives two male assemblies, such as to be described further below, at two sides facing away from one another.

FIG. 2A shows the different parts of a connector 8 in an exploded view. The basic components are the male assembly 10 and the female assembly 12. The female assembly 12 comprises a one-sided port 12* that basically may consist of a block of (synthetic or metallic) material into which two circular recesses 14A, 14B have been worked. The first circular recess 14A has a flat bottom wall 16 including a through-bore 18 for accommodating a continuation fluid conduit (not shown here). The second circular recess 14B has an internal thread 20 that is designed and configured to mate with an external thread foreseen at the stepped member as the force-transmitting member of the male assembly 10 to be discussed further below so as to facilitate a releasable interlocking function between the male and female assemblies 10, 12. A transition between the first and second circular recesses 14A, 14B tapers conically in the embodiment shown. It will, however, be appreciated by a skilled practitioner that the transition might also be designed in a different manner, such as substantially rectangular, for instance.

The male assembly 10 is comprised basically of four different elements. At the core of the male assembly 10 is a capillary conduit 22, such as a capillary tube. An example of such conduit 22 would be a fused silica capillary, PEEKsil™ capillary or polyimide-clad fused silica capillary, a part of which is shown in FIG. 2A. Inner bore diameters may be in the range of several micrometers, such as ten or twenty micrometers reaching up to several hundreds of micrometers depending on the intended field of application. A sealing gasket 24 of substantially cylindrical shape is provided to be arranged on the front end of the capillary conduit 22. The sealing gasket 24 may be made from any material that is deformable so that it is able, upon compression, to reliably seal two abutting surfaces, such as the flat bottom wall 16 of the first circular recess step in the one-sided port 12* and the front end of the male assembly 10. In preferred examples, the sealing gasket 24 is created in such a way as to prevent any material from coming into contact with the flow stream in the bore of the capillary conduit 22 which would run the risk of contaminating any working fluid therein. In the embodiment shown, the sealing gasket 24 has a stepped front end 24* which provides for some space in the radial direction into which deformed gasket material may be accommodated upon compression, thereby preventing any outward bulging of the deformed gasket body that might hamper the sealing effect.

A lasting joint can be established between the capillary conduit 22 and the sealing gasket 24 by gluing them together via the radially outward and inward facing opposing circumferential surfaces, respectively. Other embodiments may employ laser welding where a part of the material at the radially opposing circumferential surfaces of the two elements to be jointed is exposed to electromagnetic radiation, such as laser light, so that it becomes partially molten and establishes an adhesive bond between the two contacting opposing surfaces upon re-hardening. Other ways of creating a joint are heating the complete body (or bodies) or just the surface(s) to be jointed and then fusing them together with the corresponding counterpart by heat, molding, infrared radiation etc.

Further provided is a stepped member 26 as the force-transmitting member having an internal passage 28 through which the capillary conduit 22 is bound to reach. In the embodiment shown, the passage 28 has basically two sections; a first section 28A of narrow inner diameter dimensioned such as to closely but slidably accommodate the capillary conduit 22 and a second section 28B of larger inner diameter. The transition 28C between the first section 28A and second section 28B may comprise a perpendicular edge or, as illustrated, a slight conical taper. The edge at the transition 28C in the passage 28 of the stepped member 26 may interact with a particular coating layer or additional protective tubing (not shown here) on parts of the capillary conduit 22, thereby facilitating a limit stop that limits the axial movability of the stepped member 26 relative to the capillary conduit 22 which improves the handling of a connector thusly devised.

Viewed from outside, the stepped member 26 in the embodiment shown has three basic portions. The first portion 26A is of smallest outer diameter being similar to that of the sealing gasket 24, and generally takes the form of an annular cylindrical protrusion standing out from the rest of the stepped member 26. The second portion 26B of larger outer diameter features an external thread 30 at its outer circumferential surface that is bound to mate with the internal thread 20 at the second recess step 14B in the one-sided port 12* as described above. The third portion 26C has the largest outer diameter and serves as the finger tightening portion at which an operator may screw the male assembly 10 into the female assembly 12 by turning. The dimensions of this third portion 26C are preferably chosen such that easy manual handling by an operator is facilitated. An outer diameter of the third portion 26C may be in the millimeter range, such as between six and seven millimeters, for example, but can generally be chosen by a skilled practitioner as is deemed fit.

The last element of the male assembly 10 is a jacket 32 that is generally of annular cylindrical shape and may be made of any rigid and dimensionally stable material, such as stainless steel, for example. The jacket 32 has an inner diameter adapted to closely accommodate the sealing gasket 24. The jacket 32 and the sealing gasket 24 are jointed to one another via their radially inward and outward facing circumferential surfaces, respectively. One embodiment includes a swage joint between jacket 32 and sealing gasket 24. Other embodiments may be of adhesive nature, or the like. It is to be noted that the dimensions of the jacket 32 and the first portion 26A of the stepped member 26 are chosen in this example such that the jacket 32 may receive the first portion 26A slidably, that is facilitating axial guidance and alignment but without substantially inhibiting any axial motion between the two. It is further to be noted that the axial lengths of the sealing gasket 24, jacket 32 and first portion 26A of the stepped member 26 are chosen such that, when the connection between the male and female assemblies 10, 12 is established, the rearward facing front end of the jacket 32 stays clear from the transition between the first and second portion 26A, 26B of the stepped member 26 (shown as perpendicular in the instant example).

FIG. 2B (to the right of FIG. 2A) shows the male assembly 10 put together and ready for being inserted into the one-sided port 12* of the female assembly 12. As can be seen, a short part of the front end of the sealing gasket 24 stands out from the front end of the capillary conduit 22 as well as from that of the co-extensive jacket 32 thereby rendering that part one which will contact the flat bottom wall 16 in the one-sided port 12* first upon insertion of the male assembly 10 into the female assembly 12, and will be deformed. A skilled practitioner will appreciate, however, that the sealing gasket 24 could be designed and arranged on the capillary conduit 22 such that its front end comes to lie substantially flush with the front end of the former. The sealing would then be effected as soon as the front ends of the three elements capillary conduit 22, sealing gasket 24 and jacket 32 substantially simultaneously come into contact with the flat bottom wall 16 of the one-sided port 12* upon insertion.

FIG. 2C (to the right of FIG. 2B) shows the connection between the male and female assemblies 10, 12 of FIGS. 2A and 2B when the internal and external threads 20, 30 of the second recess step 14B in the one-sided port 12* and the second portion 26B of the stepped member 26 have been engaged with one another. The first portion 26A of the stepped member 26 as the force-transmitting member exerts axial compressing forces directly on the sealing gasket 24 that contacts the flat bottom wall 16 of the first recess step 14A in the one-sided port 12*, becomes deformed as a result and thereby seals this interface such that no fluid can escape the inner bore of the capillary conduit 22 radially but will rather flow forward into the adjacent connection tubing 34 foreseen in the through-bore 18 of the one-sided port 12*. This design renders the pressurization forces being exerted very homogeneously about the circumference of the sealing gasket 24 and thereby allows for a very tight and reliable seal, suited for high pressure liquid chromatography applications often operating in a pressure range from about 50 to 350 bar or even higher, essentially without any significant dead-volume at the interface that could degrade performance, such as by sample carry-over.

A skilled practitioner will appreciate that one beneficial effect, among others, of the dimensionally stable jacket 32 surrounding the deformable sealing gasket 24 and comparatively delicate capillary conduit 22 is to prevent axial pressurization forces exerted on the sealing gasket 24 from being partially dissipated in radial outward directions which would weaken the pressure seal in the axially forward direction at the front end.

Figure 3A:
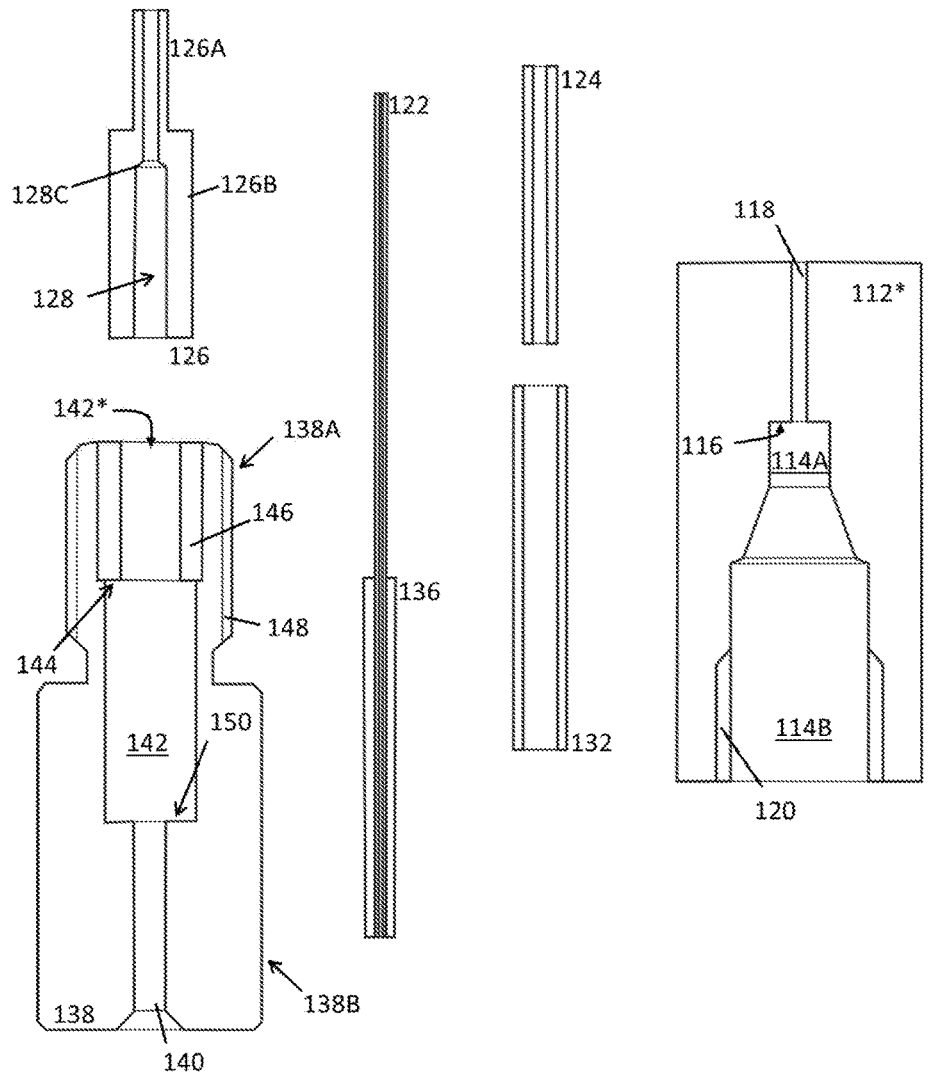
FIGS. 3A and 3B schematically depict another embodiment of a connector according to principles of the invention, with all elements disassembled (FIG. 3A) and finally in a partially assembled and fully connected state (FIG. 3B).

FIG. 3A depicts another embodiment of a fluid connector 8 according to principles of the invention. As this additional embodiment shows a certain degree of similarity with that presented with reference to FIGS. 2A to 2C, the following description will focus on the differences there-between.

FIG. 3A illustrates the different elements of a connector disassembled and placed next to one another. The one-sided port 112* (rightmost) of the female assembly shows basically a block of (synthetic or metallic) material into which two circular recesses 114A, 114B have been worked, similar to the one shown in FIG. 2A. The jacket 132 (bottom center right) can be made of a dimensionally stable material, such as stainless steel, and comprises a basically annular cylindrical element dimensioned such as to accommodate the sealing gasket 124 (top center right) as well as the first portion 126A of a stepped member 126 (top leftmost) as the force-transmitting member. The sealing gasket 124 is itself an annular cylindrical element in this example, without any stepped front end. In the embodiment shown, the front end of the sealing gasket 124 is bound to be arranged flush with that of both the capillary conduit 122 (center left) as well as that of the jacket 132, as will be explained further below.

The connector comprises a capillary conduit 122 which in this example is further provided with a coating layer 136 (or additional protective tubing) that reaches up to a point spaced apart some distance from the front end of the capillary conduit 122. The coating layer 136 allows for a bulkier design of upstream parts of the capillary conduit 122 and is intended to function as a limit stop when being inserted into the passage 128 in the stepped member 126 to be further discussed below. In so doing, the axial movability of the stepped member 126 in relation to the capillary conduit 122 can be limited, allowing for easier handling of the male assembly. It basically prevents certain individual elements of the assembly from accidentally falling apart.

The stepped member 126 in the instant embodiment has a first portion 126A of substantially annular cylindrical shape that resembles that (26A) of the stepped member 26 described with reference to the embodiment in FIGS. 2A to 2C. The second portion 126B of the stepped member 126B, however, is in this example merely of annular cylindrical shape, too, without any additional features, such as an external thread (30) to enable an interlocking function. The passage 128 contained in the stepped member 126 has two distinct sections; one of small diameter that closely but slidably receives the capillary conduit 122 without coating layer 136, whereas the other has a larger diameter dimensioned such as to slidably receive the capillary conduit 122 with the coating layer 136. The transition 128C between the two sections may interact with the coating layer 136 thereby limiting the axial movability as described above.

The most notable difference between the previous embodiment described with reference to FIGS. 2A to 2C and the instant embodiment is the presence of an additional element, namely a hollow handling shell 138 (bottom leftmost). The hollow handling shell 138 comprises an internal passage 140 for closely but slidably accommodating the capillary conduit 122 with coating layer 136 which discharges into a cavity 142 of larger diameter that is dimensioned such as to slidably receive the second portion 126B of the stepped member 126. The cavity 142 may comprise an opening 142* the inner diameter of which is constricted such as to provide for an inward-reaching edge 144 with which a front edge of the second portion 126B of the stepped member 126 may engage in order to prevent it from accidentally falling out. The constriction can be brought about as shown by an annular cylindrical insert 146 put into the opening 142* of the cavity 142, for instance.

Viewed from outside, the hollow handling shell 138 has two distinct sections. The first section 138A has an outer diameter that is adapted to substantially match the inner diameter of the second recess step 114B of the one-sided port 112*, and further comprises an external thread 148 which is configured to mate with the internal thread 120 foreseen at the second recess step 114B of the one-sided port 112* such as to allow for releasable interlocking between the male and female assemblies 110, 112 of this embodiment.

The second section 138B of the hollow handling shell 138 has a larger outer diameter and is designed and configured such as to be easily manually actuated so that it can serve as a finger tightening section. The outer circumferential surface of this second section 138B may, for example, be textured in order to render a positive haptic feedback when being touched by an operator.

Thus, it can be seen that, during the putting together of the male assembly 110, the second portion 126B of the stepped member 126 is inserted into the cavity 142 of the hollow handling shell 138 and subsequently kept in place by the annular constriction cylinder 146 located at the opening 142* of the cavity 142. The capillary conduit 122 is inserted from behind into the passages 140, 128 of both the hollow handling shell 138 as well as the stepped member 126 and reaches there-through so that it stands out from the front end of the first portion 126A of the stepped member 126. Then, the sealing gasket 124 may be arranged at the front end of the capillary conduit 122 and jointed thereto as has been indicated previously. The jacket 132 is finally put over the sealing gasket 124 and first portion 126A of the stepped member 126 until its front end comes to lie substantially flush with those of the capillary conduit 122 and jacket 132. As before, the jacket 132 is jointed rigidly merely to the underlying sealing gasket 124 but not to the first portion 126A of the stepped member 126 which it merely slidably surrounds in the example shown thereby retaining some degree of motional freedom.

In this exemplary male assembly 110, axial motion of the stepped member 126 relative to the hollow handling shell 138 is limited by the ground wall 150 of the cavity 142 in the backward direction as well as the constriction of the cavity opening 142* in the forward direction. Similarly, axial motion of the capillary conduit 122 in relation to the rest of the male assembly is limited by the transition 128C between the large and smaller diameter section of the passage 128 in the stepped member 126 (interacting with the coating layer 136 or additional protective tubing) in the forward direction as well as the contacting opposing front ends of the first portion 126A of the stepped member 126 and the sealing gasket 124, to which it is firmly jointed, in the backward direction.

Figure 3B:
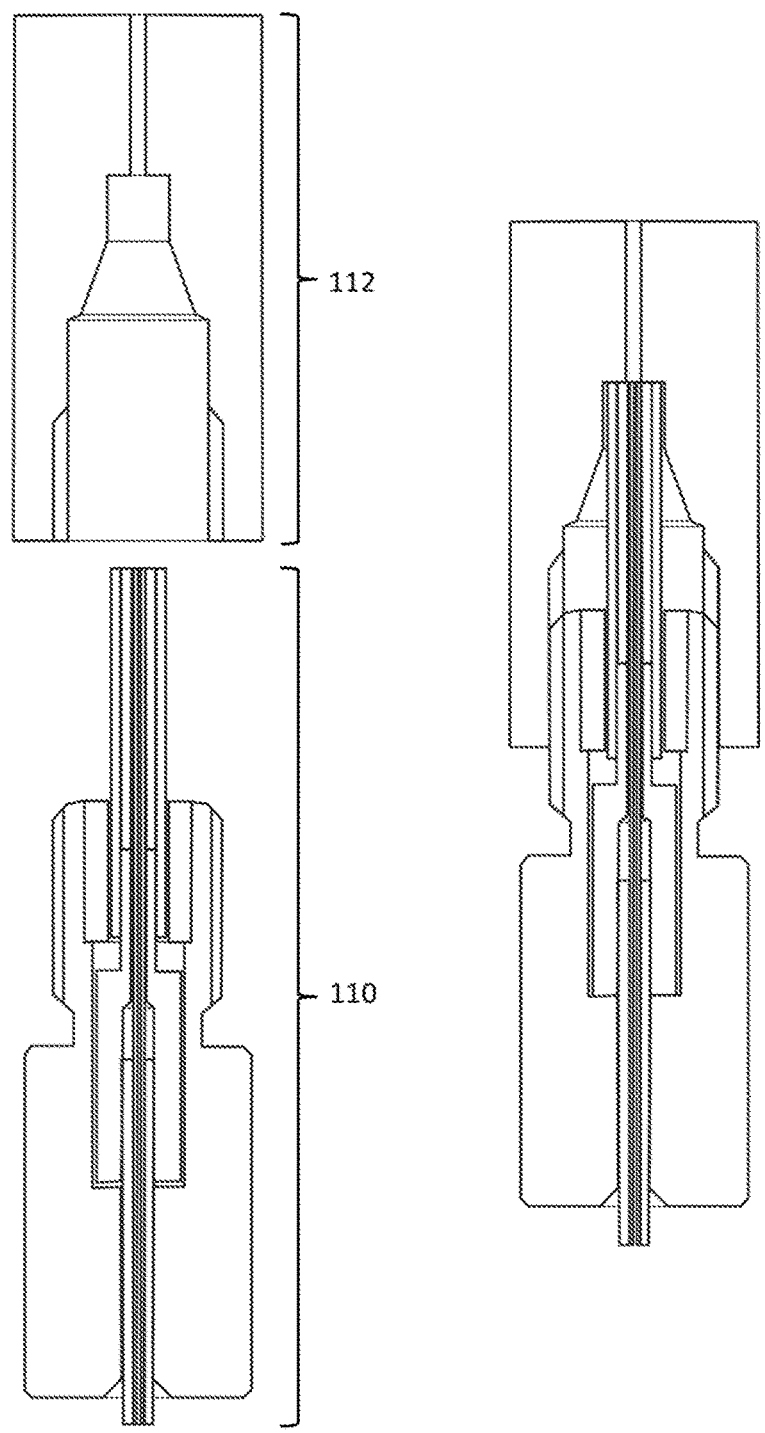

FIG. 3B shows the male and female assemblies 110, 112 of the additional embodiment from FIG. 3A (i) put together individually but disconnected from one another on the left hand side, and (ii) in an engaged condition on the right hand side where the front end of the male assembly 110 contacts and is, in fact, pressed against the bottom wall 116 of the first recess step 114A in the one-sided port 112* of the female assembly 112 allowing a chromatography fluid flowing through the inner bore of the capillary conduit 122 to be transmitted further on through tubing to be accommodated in the through-bore 118 of the one-sided port 112* but not shown here for the sake of clarity.

As has been described before with reference to the embodiments in FIGS. 2A to 2C, the first portion 126A of the stepped member 126 as the force-transmitting member exerts axial compressing forces directly on the sealing gasket 124 that contacts the flat bottom wall 116 of the first recess step 114A in the one-sided port 112*, due to the flush alignment together with the front ends of the capillary conduit 122 and the jacket 132, so that this interface is sealed such that no fluid can escape the inner bore of the capillary conduit 122 radially but will rather flow forward into the adjacent connection tubing (not shown) bound to be accommodated in the through-bore 118 of the one-sided port 112*. Also this slightly altered design renders the pressurization forces being exerted very homogeneously about the circumference of the sealing gasket 124 and thereby allows for a very tight and reliable seal, suited for high pressure liquid chromatography applications—HPLC, essentially without any significant dead-volume at the interface that could degrade performance, such as by sample carry-over as set out before.

Figure 4:
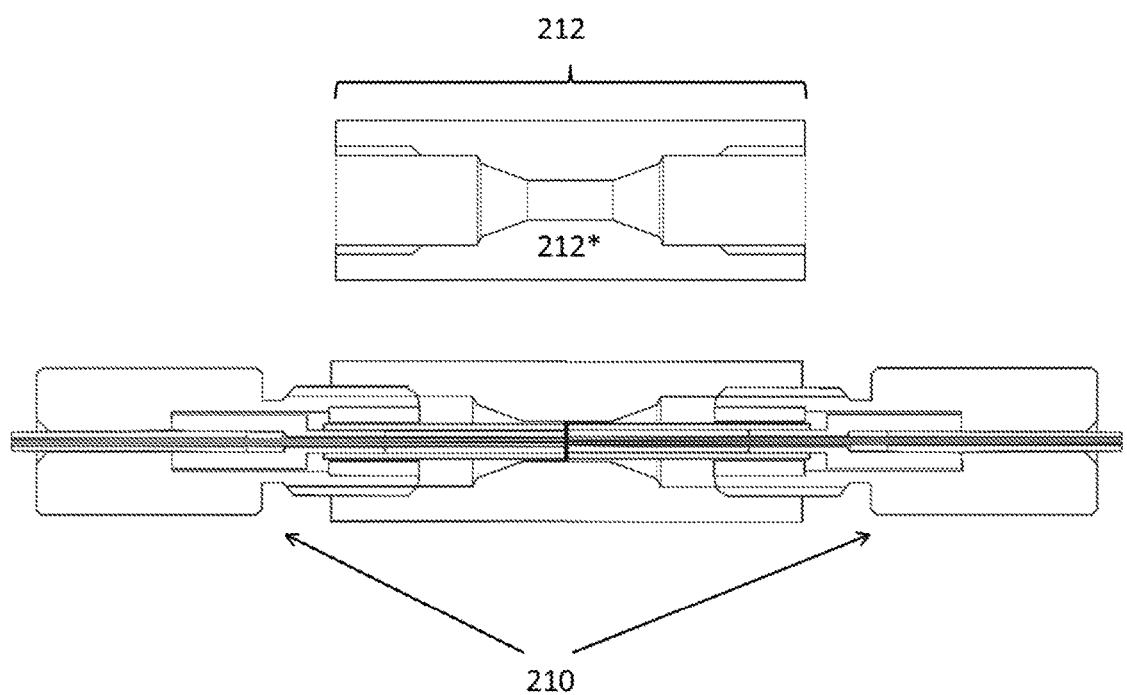
FIG. 4 shows a female assembly with receiving member that takes the shape of a double-sided union.

The example implementations from FIGS. 2A to 2C and 3A to 3B referred to above show a one-sided port 12*, 112* to which a male assembly 10, 110 is coupled on only one side thereof, correlating somehow to the depiction in FIG. 1A. Departing from this one-sided approach and rather correlating to the sketch in FIG. 1B, FIG. 4 illustrates schematically a female assembly that comprises a receiving member which is accessible to male assemblies 210 at two (opposing) sides thereof, forming a double-sided union 212*. In other words, the capillary conduit of one of the male assemblies 210 abuts the respective other one and thereby represents the continuation conduit of the respective other male assembly 210 in this example and vice versa. In the embodiment shown, the double-sided union has a symmetric design in that both recesses have the same size and geometry. A skilled practitioner would understand that also asymmetric designs are conceivable, such as recesses configured for receiving different male assemblies.

In the example of FIG. 4, however, the two male assemblies 210 have the same exemplary design as that shown in FIGS. 3A and 3B, though a skilled practitioner will understand that this embodiment is not to be understood restrictively. Favorably, the axial extension of the two internal threads at the respective second recess steps are dimensioned such that, when the male assemblies 210 have been screwed into the receiving member to the maximum, the respective front ends come to lie at about the center of the union piece 212* as shown, thereby ensuring reliable radial guidance during the insertion.

Figure 5:
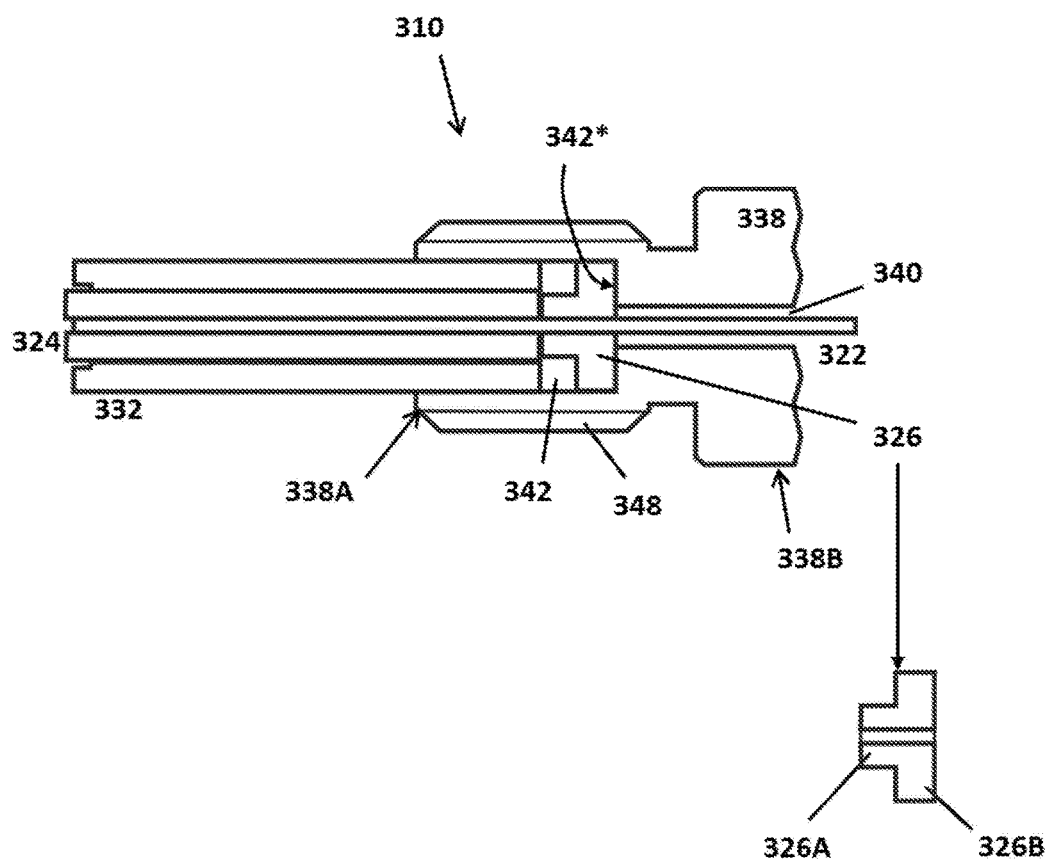
FIG. 5 depicts a connector variant basically having different designs of the stepped member as well as the hollow handling shell.

FIG. 5 shows a truncated view of a male assembly 310 having a slightly different configuration than that illustrated in the FIGS. 2 to 4. For the sake of clarity, no female assembly is shown in FIG. 5, it being understood though that the male assembly 310 depicted would be compatible basically with any of the female assemblies shown in the other embodiments, as the case may be, after some minor structural and dimensional adaptation.

As can be seen, the male assembly 310 comprises a capillary conduit 322, a sealing gasket 324 (slightly protruding), a jacket 332 (having a slightly inwardly stepped front end in order to accommodate deformed sealing gasket material) and a short stepped member 326 as the force-transmitting member. Similar to the embodiment of FIGS. 3A and 3B, the male assembly 310 has a hollow handling shell 338 with an internal passage 340 for receiving the capillary conduit 322 which discharges into a cavity 342 of larger diameter that is dimensioned such as to slidably receive the second portion 326B of the stepped member 326 (shown isolated at the bottom right) and long enough to partly slidably accommodate the conduit-gasket-jacket arrangement shown, which also provides for axial guidance and alignment. The stepped member 326 takes here the shape of a T-shaped washer (from a lateral cross section view at bottom right). Other shapes than T-shaped are also conceivable, however.

As before, viewed from outside, the hollow handling shell 338 has two distinct sections. The first section 338A comprises an external thread 348 which is configured to mate with an internal thread foreseen at a suitable receiving member such as to allow for releasable interlocking. The second section 338B of the hollow handling shell 338 has again a larger outer diameter and is designed and configured such as to be easily manually actuated so that it can serve as a finger tightening section, for instance.

In contrast to previous embodiments, there is no cylindrical protrusion from the stepped member body being inserted from rearward into the jacket 332 and directly contacting a rearward facing surface of the sealing gasket 324 for exerting axial pressurization thereto. Rather, the rearward facing front end of the sealing gasket 324 being aligned about flush with the rearward facing front end of the jacket 332 directly contacts the forward facing front end of the first portion 326A of the stepped member 326 for being directly axially pressurized thereby. In the process of inserting the male assembly 310 illustrated into a female assembly, it may happen, of course, that the first portion 326A compresses the rear part of the sealing gasket 324 such that it reaches slightly into the cylindrical space formed within the jacket 332.

Figure 6:
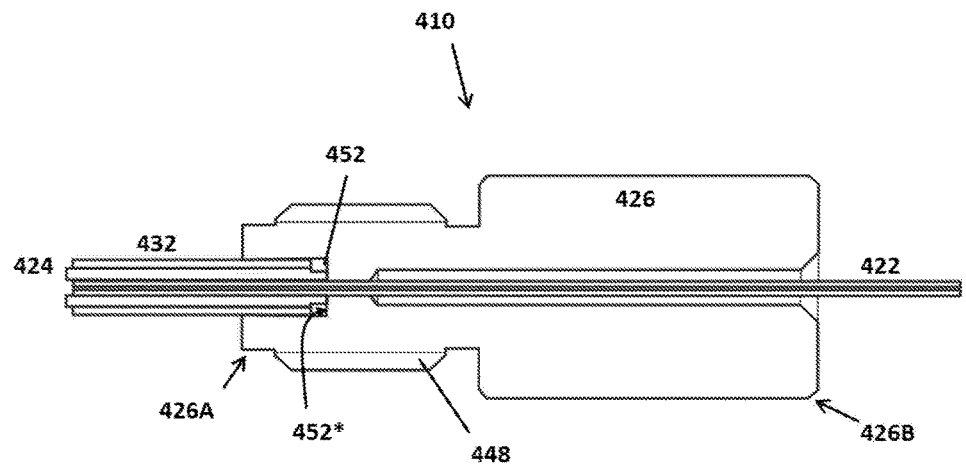
FIG. 6 illustrates another design variant of a connector according to principles of the invention.

FIG. 6 depicts a further embodiment of a male assembly 410 having a configuration slightly different from those illustrated previously. For the sake of clarity, again no female assembly is shown in FIG. 6, it being understood though that the male assembly 410 depicted would be equally compatible basically with any of the female assemblies shown in the other embodiments, as the case may be, after some minor structural and dimensional adaptation.

As can be seen, the male assembly 410 comprises a capillary conduit 422, a sealing gasket 424 (slightly protruding), a jacket 432 and a stepped member 426 as the force-transmitting member with a first portion 426A and an adjacent second portion 426B.

In contrast to embodiments previously described, instead of taking the shape of a cylindrical protrusion from the remainder of the stepped member 426 that becomes accommodated within a rear part of the hollow cylindrical jacket 432, the first portion 426A of the stepped member 426 according to FIG. 6 has a cylindrical recess 452 into which the arrangement of capillary conduit 422, sealing gasket 424 and jacket 432 is partly slidably accommodated. The sealing gasket 424 is not covered or surrounded by the jacket 432 along its full axial extension. At the front end, for example, the sealing gasket 424 slightly protrudes from the jacket 432 and capillary conduit 422, to be compressed when contacting a bottom surface or a front end of another male assembly in the receiving member, similar to some of the embodiments described further above.

Here however, also at the rear end does the sealing gasket 424 extend slightly beyond the end face of the jacket 432 and, when fully received in the recess 452 in the first portion 426A, abuts a forward facing ground surface 452* of the recess 452. In this manner, the male assembly 410 can be axially pressurized where the axial forces are conveyed directly into and through the sealing gasket 424, without taking a detour via any intermediate elements. The jacket 432 being properly dimensioned merely provides for axial alignment and guidance within the recess 452 of the first portion 426A. At the outer circumference, the first portion 426A of the stepped member 426 may have an external thread 448 as indicated, compatible to an internal thread foreseen at the corresponding counter-surface in the receiving member (not shown). The second portion 426B of the stepped member 426 may serve as a finger tightening portion, as has been described before with the respect to some of the other connector embodiments.

Figure 7A:
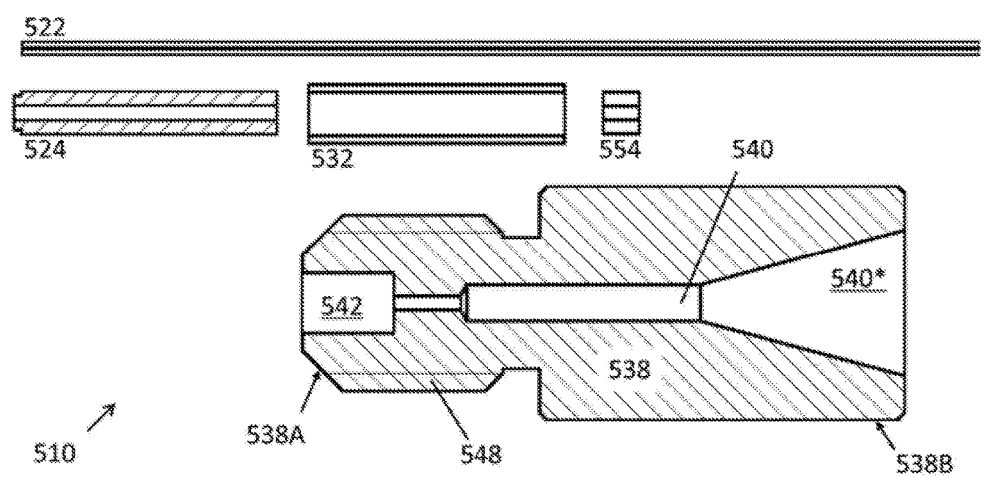
FIGS. 7A and 7B show yet another design variant of a connector according to principles of the invention.

FIG. 7A illustrates another embodiment of a fluid connector according to principles of the invention. As this further embodiment shows a certain degree of similarity with that presented with reference to FIG. 6, the following description will focus on the differences there-between.

FIG. 7A shows the different elements of a male assembly 510 disassembled and placed next to one another. The jacket 532 can be made of a dimensionally stable material, such as stainless steel, and comprises a basically annular cylindrical element dimensioned such as to accommodate the sealing gasket 524 that takes the form of an annular cylindrical element comprising a stepped front end. A force-transmitting member 554 takes the form of a short annular cylinder in this example, the inner width of which being adapted to slidably receive a capillary conduit 522 within and the outer diameter of which being dimensioned such as to being slightly undersized compared to an inner diameter of the jacket 532. In the embodiment shown, upon assembly, the stepped front end of the sealing gasket 524 is bound to slightly protrude from those of both the capillary conduit 522 as well as of the co-extensive jacket 532, as will be explained further below.

A difference between the previous embodiment described with reference to FIG. 6 and the instant embodiment is the presence of a hollow handling shell 538. The hollow handling shell 538 comprises an internal passage 540 for closely but slidably accommodating the capillary conduit 522 that discharges into a cavity 542 of larger diameter that is dimensioned such as to slidably receive the jacket 532. A design variant compared to previous embodiments includes a flaring rearward part 540* of the passage 540 to enable easier access at this rearward-facing side.

Viewed from outside, the hollow handling shell 538 has two distinct sections. The first section 538A has an outer diameter that is adapted to substantially match the inner diameter of a female assembly 512 to be depicted in FIG. 7B, and further comprises an external thread 548 which is configured to mate with an internal thread foreseen at this female assembly 512 such as to allow for releasable interlocking between the male and female assemblies 510, 512 of this embodiment.

The second section 538B of the hollow handling shell 538 has a larger outer diameter and is designed and configured such as to be easily manually actuated so that it can serve as a finger tightening section. The outer circumferential surface of this second section 538B may be textured in order to render a positive haptic feedback when being touched by an operator.

Figure 7B:
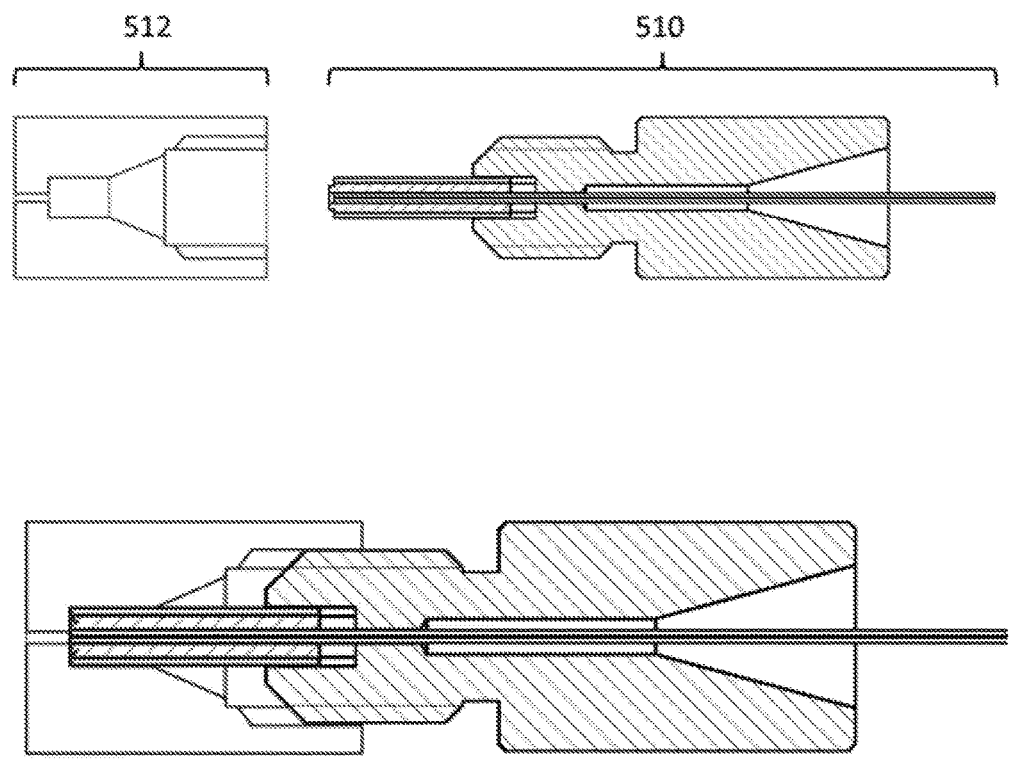

The upper panel of FIG. 7B shows the male assembly 510 put together and ready for being inserted into the female assembly 512 that takes the shape of a one-sided port in this example and resembles those described in conjunction with previous embodiments so that the particulars do not have to be repeated here.

As can be seen, the force-transmitting member 554 comes to rest in the cavity 542 of the hollow handling shell 538, while being supported in the upstream axial direction by a forward-facing wall thereof. As can be seen, the jacket 532 does not come into contact with this forward-facing wall of the cavity 542. The capillary conduit 522 is accommodated in the passage 540 of the hollow handling shell 538 and within the inner widths of both the force-transmitting member 554 as well as the sealing gasket 524. As described before, the capillary conduit 522 and the sealing gasket 524 are rigidly jointed to one another via opposing radial surfaces while the force-transmitting member 554 remains not so jointed and engages only slidably with the other elements of the male assembly 510 thereby retaining some degree of motional freedom. The jacket 532 is put over, and jointed rigidly merely to the sealing gasket 524 basically covering it along its whole axial extension. As has been indicated above, the stepped front end of the sealing gasket 524 slightly protrudes from the front end of the jacket 532, ready to be deformed by a counter-surface in the female assembly 512 upon insertion.

The lower panel of FIG. 7B shows the male and female assemblies 510, 512 previously described in an engaged condition where the front end of the male assembly 510 contacts and is, in fact, pressed against the bottom wall of a first recess step in the one-sided port of the female assembly 512 allowing a chromatography fluid flowing through the inner bore of the capillary conduit 522 to be transmitted further on through tubing to be accommodated in the through-bore of the one-sided port but not shown here for the sake of clarity.

As has been described before with reference to various earlier embodiments, the annular cylindrical force-transmitting member 554 exerts axial compressing forces directly on the likewise annular cylindrical sealing gasket 524 that contacts the flat bottom wall of the first recess step in the one-sided port thereby sealing this interface such that no fluid can escape the inner bore of the capillary conduit 522 radially but will rather flow forward into the adjacent connection tubing (not shown) bound to be accommodated in the through-bore of the one-sided port. Also this slightly altered design facilitates the pressurization forces to be exerted very homogeneously about the circumference of the sealing gasket 524 and thereby allows for a very tight and reliable seal, suited for high pressure liquid chromatography applications—HPLC, essentially without any significant dead-volume at the interface that could degrade performance, such as by sample carry-over as set out before.

In the above-explained embodiments, a pair of mating threads is used to deliver the releasable interlocking function between the male and female assemblies. A skilled practitioner will understand, however, that this function can be achieved in many other suitable ways, such as by a bayonet fitting, for example.

The invention has been shown and described with reference to a number of different embodiments thereof. It will be understood, however, that various aspects or details of the invention may be changed, or various aspects or details of different embodiments may be arbitrarily combined, if practicable, without departing from the scope of the invention. Generally, the foregoing description is for the purpose of illustration only, and not for the purpose of limiting the invention which is defined solely by the appended claims.

What is claimed is:

1. A connector for fluid chromatography having a female assembly including a receiving member being designed and configured to receive, and releasably interlock with, a male assembly, the male assembly comprising:
   a force-transmitting member for exerting axial pressurization;
   a capillary conduit slidably accommodated in a passage in the force-transmitting member for transmitting chromatography fluid;
   a sealing gasket surrounding a front end of the capillary conduit, the sealing gasket having a rearward facing surface located such as to directly contact a forward facing surface of the force-transmitting member for being subjected to axial pressurization thereby; and
   a jacket surrounding the sealing gasket for providing axial guidance and alignment thereto.

2. The connector of claim 1, wherein the force-transmitting member comprises a stepped member having a first portion for exerting axial pressurization featuring a first outer diameter, and having a second axially adjacent portion featuring a second outer diameter being larger than the first outer diameter.

3. The connector of claim 2, wherein the forward facing surface is located at a front end of the first portion of the stepped member, the first portion being dimensioned such by axial length and diameter that it can be largely slidably received within a rear part of the jacket.

4. The connector of claim 3, wherein a shape of the sealing gasket, the first portion of the stepped member and the jacket is substantially annular cylindrical.

5. The connector of claim 2, further comprising a third portion being located axially adjacent to the second portion of the stepped member for finger tightening a connection between the male and female assemblies, a third outer diameter of the third portion being larger than that of both the first and second portions.

6. The connector of claim 2, wherein axial lengths of the sealing gasket, the first portion of the stepped member and the surrounding jacket are dimensioned such that a rearward-facing end of the jacket stays clear from a transition between the first portion and second portion of the stepped member.

7. The connector of claim 2, further comprising a constriction foreseen in the passage of the stepped member, wherein the capillary conduit has an outer coating layer or additional protective tubing at a position spaced apart from its front end, the coating layer or protective tubing being designed and configured to engage with the constriction and further having the function of a limit stop in order to limit axial movability of the stepped member relative to the capillary conduit.

8. The connector of claim 2, wherein a rearward facing front end of the sealing gasket that comprises the rearward facing surface stays free from being covered by the jacket and directly contacts a forward facing ground of a recess worked into the first portion of the stepped member with which the sealing gasket and jacket partly engage.

9. The connector of claim 1, wherein the sealing gasket stands out slightly from the front end of the capillary conduit in a disengaged condition of the male and female assemblies, and becomes compressed into a substantially flush alignment with the front end of the capillary conduit when the male and female assemblies are engaged with one another.

10. The connector of claim 9, wherein a front end of the sealing gasket is stepped such as to allow material deformation of the sealing gasket to occur substantially without any outward bulging.

11. The connector of claim 1, wherein a shape of the force-transmitting member is substantially annular cylindrical, and wherein an outer diameter of the force-transmitting member is slightly undersized compared to that of the sealing gasket.

12. The connector of claim 1, wherein the receiving member is one of a one-sided port and a double-sided union.

13. The connector of claim 12, wherein the one-sided port has a doubly stepped circular recess, the inner diameter of the first recess step being adapted to the outer diameter of the jacket, and the inner diameter of the second recess step being larger than that of the first recess step.

14. The connector of claim 13, wherein both the second recess step and the second portion of the stepped member have complementary interlocking mechanisms.

15. The connector of claim 12, wherein the one-sided port has an axial through-bore located such that it comes to rest in opposing relation to the front end of the capillary conduit when the male and female assemblies are engaged with one another.

16. The connector of claim 12, wherein the one-sided port has a substantially flat bottom against which a front end of the male assembly is pressed when the male and female assemblies are engaged with one another.

17. The connector of claim 1, wherein the sealing gasket is jointed radially outward to the jacket as well as radially inward to the capillary conduit via opposing outward-facing and inward-facing surfaces, respectively.

18. The connector of claim 17, wherein the joint is, or the joints are, produced by one of adhesive, radial swaging, radial plastic deformation, hammering, and laser welding, or any combination of these techniques.

19. The connector of claim 1, further comprising a hollow handling shell into which the force-transmitting member is partly accommodated.

20. The connector of claim 19, wherein the hollow handling shell comprises a first section with an interlocking mechanism designed and configured to cooperate with a complementary interlocking mechanism foreseen at the receiving member, and further comprises a second section for finger tightening the male assembly in the female assembly.

* * * * *